US012653433B2

(12) United States Patent
Kim

(10) Patent No.: US 12,653,433 B2
(45) Date of Patent: Jun. 16, 2026

(54) METHOD FOR DETECTING PHYSICAL PROPERTIES OF URINE, URINATION, AND FECES FOR DETERMINATION OF HEALTH CONCERNS BY ANALYZING URINE BUBBLES DATA IN MULTIPLE URINATION SESSIONS

(71) Applicant: Hong Min Kim, Stouffville (CA)

(72) Inventor: Hong Min Kim, Stouffville (CA)

( * ) Notice: Subject to any disclaimer, the term of this patent is extended or adjusted under 35 U.S.C. 154(b) by 237 days.

(21) Appl. No.: 18/445,550

(22) Filed: Oct. 11, 2023

(65) Prior Publication Data

US 2025/0120633 A1    Apr. 17, 2025

(51) Int. Cl.
| | |
|---|---|
| *A61B 5/20* | (2006.01) |
| *A61B 5/00* | (2006.01) |
| *E03D 9/00* | (2006.01) |
| *G01N 33/483* | (2006.01) |
| *G01N 33/493* | (2006.01) |
| *G16H 10/40* | (2018.01) |

(52) U.S. Cl.
CPC .............. *A61B 5/20* (2013.01); *A61B 5/743* (2013.01); *A61B 5/7475* (2013.01); *E03D 9/00* (2013.01); *G01N 33/4833* (2013.01); *G01N 33/493* (2013.01); *G16H 10/40* (2018.01)

(58) Field of Classification Search
None
See application file for complete search history.

(56) References Cited

U.S. PATENT DOCUMENTS

| | | | | |
|---|---|---|---|---|
| 7,148,070 B2 * | 12/2006 | Minter | ................ | G01N 33/528 |
| | | | | 436/164 |
| 10,605,717 B2 * | 3/2020 | Spangenberg | ......... | G01N 15/14 |
| 2021/0389250 A1 * | 12/2021 | Attar | ..................... | G01J 3/2803 |
| 2021/0401244 A1 * | 12/2021 | Kawai | ..................... | A47K 13/24 |
| 2022/0341920 A1 * | 10/2022 | Nakashima | ............ | G01N 33/52 |

(Continued)

FOREIGN PATENT DOCUMENTS

| | | | | | |
|---|---|---|---|---|---|
| CN | 105395221 B | * | 2/2018 | ......... | A61B 10/0038 |
| WO | WO-2019109515 A1 | * | 6/2019 | .......... | G01N 33/493 |
| WO | WO-2023225174 A1 | * | 11/2023 | ............. | A61B 5/208 |

*Primary Examiner* — Peter J Macchiarolo
*Assistant Examiner* — Jermaine L Jenkins
(74) *Attorney, Agent, or Firm* — David W. Wong

(57) ABSTRACT

The system determine the health condition of a person by measuring various physical properties of the urine and stool including the amount of bubbles formed on the top surface of a flush toilet, and the length of time the bubbles dissipate in urination. Also measuring the color including clearness, sound and speed of the urine, and forwarding the detected data to a logging unit of a central control processor. The logging unit contains a catalog of data of various urine bubbles physical properties of urine color, sound and speed relative to various health conditions. Analyzing the detected data to correlate with the data in the catalog in the logging unit to determine the possible health concerns of the person. The system also measures the stool physical properties including stool color, shape, physical dimensions and density to correlate the detected data with stool physical properties relative to various health conditions and to correlate with the urine determination to provide a comprehensive determination the possible health concerns of the person.

8 Claims, 3 Drawing Sheets

(56) References Cited

U.S. PATENT DOCUMENTS

2023/0129932 A1* 4/2023 Wang ................... G05D 1/0214
4/321
2023/0176080 A1* 6/2023 Kapp-Barnea ....... A61B 10/007
422/82.09

* cited by examiner

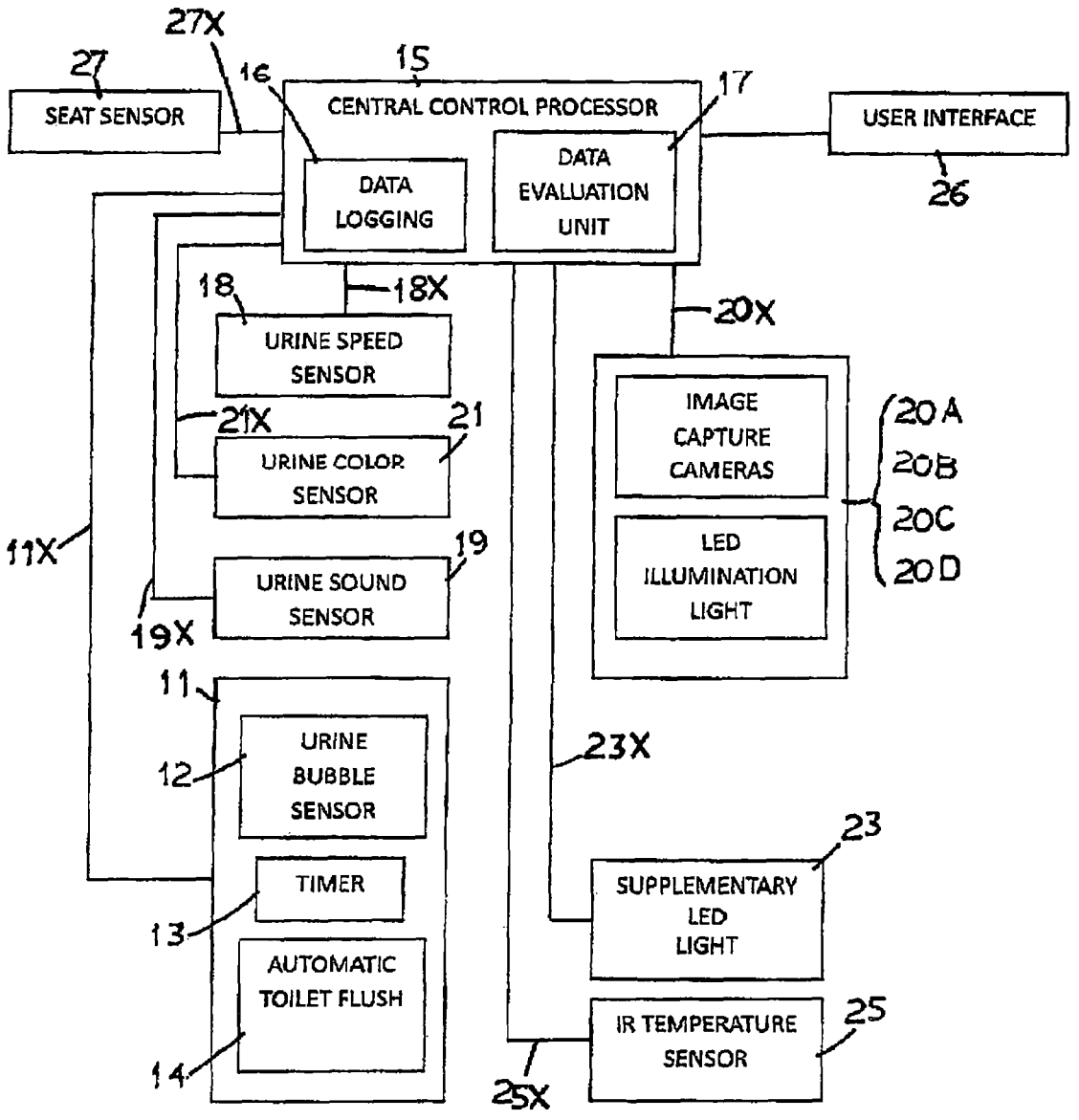
F I G U R E   1

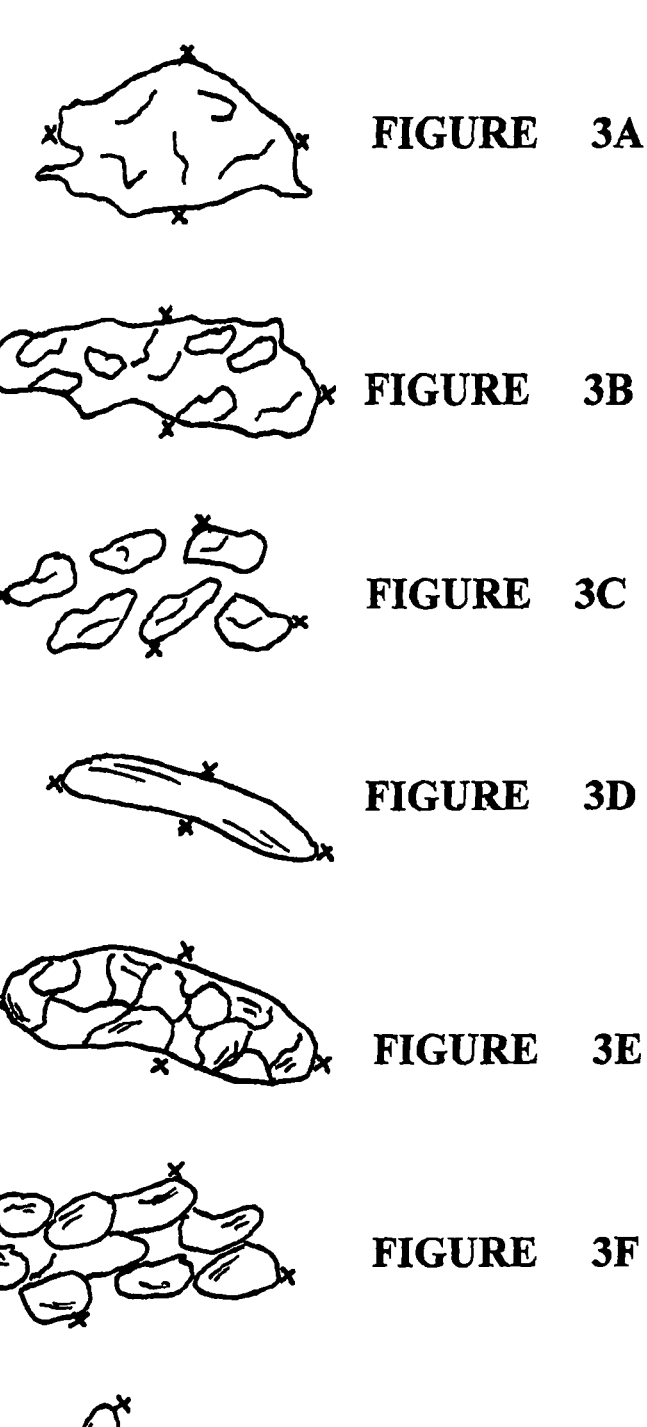
FIGURE    3A
FIGURE    3B
FIGURE    3C
FIGURE    3D
FIGURE    3E
FIGURE    3F
FIGURE    3G

METHOD FOR DETECTING PHYSICAL PROPERTIES OF URINE, URINATION, AND FECES FOR DETERMINATION OF HEALTH CONCERNS BY ANALYZING URINE BUBBLES DATA IN MULTIPLE URINATION SESSIONS

BACKGROUND OF THE INVENTION

1. Field of the Invention

This invention relates to a system for detecting various physical properties of urine, urination and faeces for determination of possible health concerns.

2. Background Art

Health monitoring and early detection of health issues are essential for promoting overall well-being and preventing the progression of numerous medical conditions. Traditional methods of health assessment often lack precision and timely detection. The present invention aims to overcome these limitations by providing a comprehensive and automated system that detects analyzes the physical properties of the urine, urination and faeces to identify potential health concerns.

Urine properties such as the amount of urine bubbles formed on the water surface of the toilet bowl when one urinates into a flush toilet and also the color, smell and appearance of urine normally can vary widely due to changes in life style, food diet, and amount of water being consumed; furthermore, these urine properties can also provide distinctive indications of the amount of protein in the urine which provides clear indication of many health conditions such as potential urinary infection, kidney infection, dehydration, diabetes, to heart disease. Also, the physical properties of urination such as the sound and speed or flow rate of urination when urine is deposited into toilet bowl can provide indications of urinary tract and bladder problems and particularly prostate problem in males.

Similarly, physical properties of faeces such as stool color and shape can also vary widely due to changes in life style, and food diet. Normally, stools are light to dark brown in color, semi-solid in texture, and sausage shaped with a mucous coating containing dead red blood cells and digested food wastes. The color of stools can also vary widely due to many different health conditions.

Many systems have been designed to monitor the color of stools and/or urine to provide guidance to people regarding health condition and concerns.

U.S. Pat. No. 10,376,200 issued on Aug. 13, 2019 to Hong Min Kim, the applicant of this patent application, shows an apparatus including sensors installable on the seat of a flush toilet for detecting the color, shape and texture of the stools to provide guidance to a user in health condition and potential health concerns.

U.S. Patent Application US2016/0223551 A1 to S. Kizuka et al published on Aug. 16, 2016 describes a system which retrieve gas emitted by stools for analysis to provide health indications to the user.

Korean Patent application KR20170051960 published on 2017 May 12 shows a method of providing sensors mounted on a bidet for obtaining urine color and stools color, shape, and weight to forward to a mobile phone. Detector is mounted on the body of the user also provides the pulse rate and oxygen level of the user to the mobile phone. A software program is provided in the mobile phone for analyzing the information to provide health indication and concerns to the user and the medical provider of the user.

SUMMARY OF THE INVENTION

It is a principal object of the present invention to provide a system for detecting a plurality of physical properties of urine and urination to provide a determination of possible health concerns.

It is another object of the present invention to provide a system in identifying male and female urination processes. Understanding gender-specific urination processes enable medical professionals to make more accurate diagnoses and implement tailored treatment plans. This knowledge assists to address conditions such as urinary tract infections, incontinence, and prostate disorders more effectively.

It is another object of the present invention to provide a system for detecting a plurality of physical properties of stools to provide determination of possible health concerns.

BRIEF DESCRIPTION OF THE DRAWINGS

Other objects and advantages of the present invention will become apparent from the following detailed description of the preferred embodiments thereof in connection with the accompanying drawings, in which FIG. 1 is schematic block diagram of the system of the present invention for providing health indication according to detecting physical properties of urine, urination and stools.

FIGS. 3A through 3G show various types of stools having different shapes and textures, and consistencies. FIG. 3A shows a Type 1 stool which is watery containing no solid pieces. This type of stool is relative to a person commonly having diarrhea. FIG. 3B shows a Type 2 stool which is loose and unformed and consists of fluffy pieces with rugged edges and a mushy consistency. This type of stool is also produced in diarrhea. FIG. 3C shows a Type 3 stool consists of a plurality of separate hard lumps which are hard to pass. FIG. 3D shows a normal Type 4 stool which is sausage shaped having a soft and smooth texture or consistency. FIG. 3E shows a Type 5 stool which is another normal stool having a relative larger in size and consists of a plurality of cracks on the surface. It has a moist consistency. FIG. 3F shows a Type 6 stool which is commonly produced in constipation and it consists of lumpy pieces and having a relatively large size with low moisture. FIG. 3G shows a Type 7 stool consists of a plurality of small hard lumps.

DETAILED DESCRIPTION OF THE PREFERRED EMBODIMENTS

Figure 2:
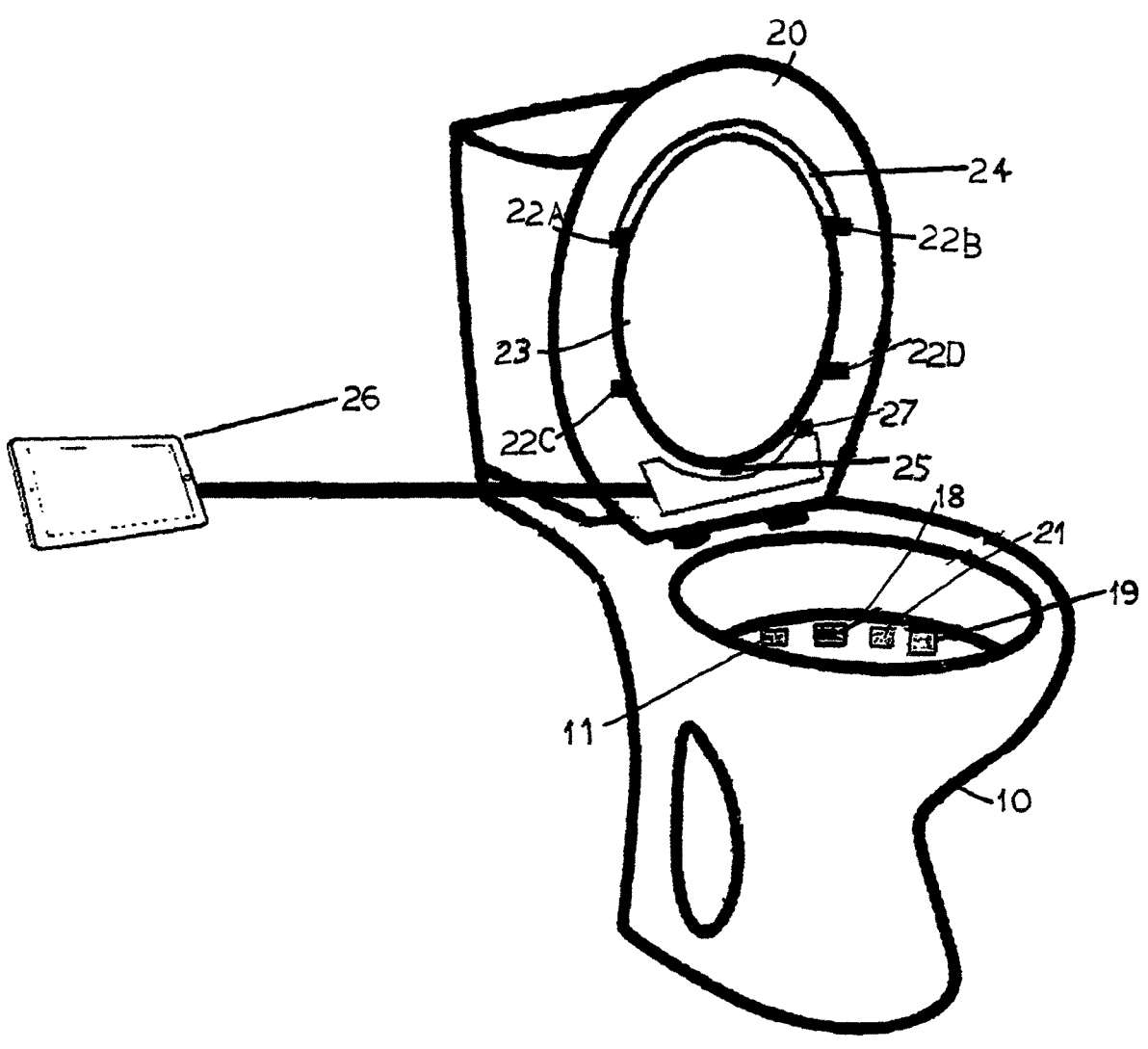
FIG. 2 is a top and side perspective view of a flush toilet according to the present invention provided with a plurality of sensors for detecting various urine, urination and/or stools physical properties for analysis to provide health determination and guidance of health concerns according to the present invention.

In urination into a flush toilet, foaming bubbles are invariably formed on the top surface of the water in the toilet due to the density of the urine, the urination force and most of all the protein content in the urine. Also, the amount of bubbles and the length of time the urine bubbles remaining on the water surface are highly dependent on the protein content in the urine which, if remaining consistently for an excessive amount of time would indicate a deteriorating condition of the kidney or potential likelihood of other diseases. Normally, if the foaming bubbles remain on the water surface for about a couple of minutes there should be no concern. According to the present invention, in a flush toilet 10, a urine image detector/processor 11 is provided at the upper inner rim of the toilet above the water top surface in the toilet. The urine image detector/processor 11 includes a urine bubble sensor 12, a timer 13, and an automatic toilet flush control 14 as best shown in the block diagram of FIG. 1. The urine image detector/processor 11 is connected to a central control processor 15 such that when the bubble image sensor 12 captures the urine bubble image formed on the water surface of the toilet bowl and forwards the bubble image to the central unit processor 15. The bubble images of consecutive urination sessions are recorded into a data logging unit 16, and the images are compared, correlated and analyzed by a data evaluation unit 17 with physical properties of urine relative to known health conditions to determine if there are health concerns. The flow of the urine, the bubbles formation and time of dissipation of the bubbles are recorded by the bubble image sensor 12 every second during urination. At a predetermined period of time of more than 5 minutes after the termination of urination the toilet bowl is flushed either manually or by an electronic or mechanical automatic flush control 14, controlled by the central control processor 15, provided at the toilet such that the toilet bowl would be flushed after a period of more than 5 minutes after the termination of urination. The deliberate time delay before flushing allows for a more thorough evaluation of the urine bubbles physical properties, which could offer valuable clues about an individual's health. It provides the information of whether the bubbles in the toilet would return to the toilet bowl during the back flow of the flush water in the toilet bowl as captured by the bubble image sensor 12. Return of bubbles in the back flow of flush water would indicate serious health problems in the kidney and/or the bladder due to high amount of protein and other organic compounds in the urine that are not filtered by the kidney. Whereas portion of the bubbles formed by dissolvable gases in the urine such as due to the force of urination deposition would dissipate quickly. Allowing time for these gases to escape ensures that the bubbles appearance is not solely due to gas content so as to pinpoint any potential underlying health issues. This precaution is taken to ensure that the analysis by the central control processor provides reliable insights into underlying health conditions that might be indicated by the presence of urine bubbles due to protein, bacteria, kidney function, and metabolic abnormalities: This step ensures that any bubble properties present in the flush water are attributed to the individual's physical properties of urination and not due to plumbing issues. The differentiation is crucial for distinguishing health related bubbles from environmental factors. By allowing bubbles to stabilize and considering the specific properties of the bubbles, the system and healthcare professionals can gain valuable insights into an individual's health status, facilitating early detection and intervention when necessary.

A urine speed sensor 18 is located at the upper inner rim portion of the toilet bowl for detecting the speed or flow rate in which the urine is being deposited in the water of the toilet bowl. A full bladder normally urinates with a greater force to produce more bubbles on the water surface due to the greater force of the urine stream. In general, a normal stream of urine has a speed or flow rate of about 15 milliliters per second. The urine speed sensor 18 also sends the urine stream speed to the central control processor 15 for correlating with urine data in the data evaluation unit 17 of the central control processor 15 for urination speed relative to various health conditions. Slow urination speed may indicate problem of enlarged prostate or bladder problem in males. The bubbles produced by the greater force of urine stream will dissipate faster than the bubbles formed due to the protein content in the urine.

A urine sound sensor 19 is also mounted at the upper rim of the toilet bowl for detecting the sound produced by the urine impacting the water in the toilet bowl and a urine color sensor 21 is also mounted at the upper inner rim portion of the toilet bowl for detecting the color of the urine. The data of the detected sound and color of the urine are forwarded to the central control processor 15 for correlating with urine physical properties relative to urine color and sound for health conditions for determining if there is any health concern for the detected sound and color characteristics or physical properties of the urine. The color of urine may vary from clear, cloudy, pale yellow, brown, blue, pink and red depending of the health condition and possibility of other diseases. Clear and pale yellow color urine indicate normal health; cloudiness may due to infections, kidney stones, or other changes in health and sometimes may be accompanied with pain or other symptoms in urination; brown may indicate urinary tract infection or deteriorating kidney function and dehydration, while pink and red color may indicate inflammation and other serious diseases including bleeding. The loudness of the sound of the urine impacting the flush water in the toilet indicates the healthiness of the urination function.

When men urinate, the sound tends to be more distinct and audible due to the force and trajectory of the urine stream, which can result in a steady and sometimes louder sound as the urine strikes the water in the toilet bowl. Whereas when female urinates it is generally characterized by a quieter sound due to the nature of the anatomical differences. The urine stream is less forceful and it does not create the same distinct splashing sound as in male. The detected sound of urination is forwarded to the central control processor 15 for the evaluation of health concerns analysis. Understanding the intricacies of gender urination processes attributes to the capability of the system of the present invention to analyse the detected urine physical properties more accurately according to the gender differences. In male, the urination process is intricately linked to the male reproductive system. The kidney filters waste products and excess fluids from the blood, producing urine that travels through the ureter to the bladder. The bladder acts as a reservoir for urine until it is expelled. Notably, the prostate gland encircles the urethra and out of the body. This process is modulated by the micturition reflux, a neural mechanism triggered by the bladder stretching. In male, the long urethra contributes to a more extended pathway for urine to traverse. This extended route may impact susceptibility to urinary tract infections and other urinary disorders. The presence of the prostate gland in males introduces a unique consideration. Prostate health is crucial, as conditions like benign prostate hyperplasia (BPH) can obstruct urine flow. Understanding the interplay between the prostate, bladder, and urethra is essential for diagnosing and treating male urinary issues.

Female possess a distinct urination process influenced by the proximity of the urinary and reproductive systems. The kidneys filter wastes, and urine flows through the ureter to the bladder. The bladder serves as a reservoir, and during urination, the urethra, a shorter structure than in male, facilitates the passage of urine outside the body. The close proximity of the urethra to the female reproductive organs can contribute to the risk of urinary tract infections. The proximity of the urethra to the vagina and anus can introduce bacteria into the urinary tract, necessitating heightened hygiene awareness. Hormonal changes associated with menstruation, pregnancy, and menopause can affect female urinary patterns. Hormones influence bladder control and may contribute to conditions like urinary incontinence. Female urination is generally characterized by a quieter sound than male due to the nature of the anatomical differences. The urine stream is less forceful and does not create the same distinct splashing sound as in male.

Stool physical properties such as the shape, consistency, physical size of the stool as well as its density also can provide an indication of the health condition of a person. Generally, there are seven types of stool shapes and consistencies as best shown in FIG. 3A to FIG. 3G. FIG. 3A shows a Type 1 stool which is watery containing no solid pieces. This type of stool is relative to a person commonly having diarrhea. FIG. 3B shows a Type 2 stool which is loose and unformed and consists of fluffy pieces with rugged edges and a mushy consistency. This type of stool is also produced in diarrhea. FIG. 3C shows a Type 3 stool consists of a plurality of separate hard lumps which are hard to pass. The type of stool usually indicates digestive problems. FIG. 3D shows a normal Type 4 stool which is sausage shaped having a soft and smooth texture or consistency. FIG. 3E shows a Type 5 stool which is another normal stool having a relatively larger in size and consists of a plurality of cracks on the surface. It has a moist consistency. FIG. 3F shows a Type 6 stool which is commonly produced in constipation and it consists of lumpy pieces and having a relatively large size with low moisture. FIG. 3G shows a Type 7 stool which is produced in very constipated condition. It consists of a plurality of small hard lumps which is extremely hard to pass.

As shown in FIGS. 1 and 2, integral imaging units 22A, 22B, 22C and 22D contain image capture cameras and LED Illumination devices, are provided at the underside of the toilet seat 20 around the opening 23 of the seat. The integral imaging units are operative for capturing the physical properties of shape, consistency and dimensions of the stools expelled from the user into the toilet bowl during bowel movement, as well as the density of the stools shown by the image of the stools whether they are submerged into or floating on the water in the toilet bowl. The detected data are forwarded to the data logging unit 16 of the central control processor 15 and the data including stools physical properties of shape, dimension, consistency and density relative to various health conditions are subsequently correlated and analyzed by the data evaluation unit 17 in the central control processor 15 together with the urine data to provide an accurate and comprehensive determination of the health condition of the user.

A supplementary LED light 24 is provided at the front edge portion of the toilet seat opening 23 to enhance the illumination of the stools and urine for the image capture cameras and the urine sensors 12, 18, 19 and 21 as well as the integral imaging units 20A through 20D.

The stool images captured by the cameras of the integral imaging units 20A through 20D are measured at various points around the peripheral of the stool images as marked with a plurality of x as shown in FIG. 3 to determine the size of the stool by the data evaluation unit 17.

An IR temperature sensor 25 is provided at the rear edge portion of the toilet seat opening 23. The IR temperature sensor 25 measures the temperature of the gas emitted from the stool. The temperature of the stool is continuously forwarded to the data logging unit 16 of the central control processor 15. Changes in the stool temperature in a plurality of bowel movements are analyzed and correlated with the analysis of the urine and stool characteristics to determined if the temperature changes are a result of possible digestion diseases.

The central control processor 15 is connected to the various sensors 11, 18, 19, 20, 21, 23, 25 and 27 either wirelessly or with a wire connections 11X, 18X, 19X, 20X, 21X, 23X, 25X and 27X respectively. A visual display and a user interface such as an input key board may be provided in a housing unit 26 for the user to enter request requests and commands into the central control processor 15.

A motion sensor 27 is provided at the underside of the toilet seat to detect the present of the person sitting on the toilet 10 for bowel movement for activating said central control processor to activate the various devices for the determination of the health condition.

What is claimed:

1. A method for detecting physical properties of urine, urination and forces and feces for determination of health concerns of a person method comprising:

having said person urinating into a flush toilet containing flush water in a toilet bowl, measuring amount of bubbles formed on water top surface of said flush water by the urine;

measuring the length of time said bubbles remaining on the water top surface of the flush toilet;

forwarding detected data of said amount of bubbles and length of time said bubbles remaining on the top surface of the water to a data logging unit located in a central control processor, measuring color including clearness of the urine in a plurality of urination sessions and forwarding detected data of said urine color to said central control processor;

measuring speed of urination forces of several urination sessions and forwarding detected data of the urination forces to said central control processor;

measuring urination forces and sound of the urine impinging on the flush water and also forwarding detected data to said central control processor;

correlating and analyzing all the above detected data in said central control processor to provide a determination of possible health concerns of the person.

2. A method according to claim 1 including the flushing the water of the toilet and detecting whether bubbles remain on the water in back flow of water in the toilet bowl to provide additional datas for determination of possible health concerns of the person.

3. A method according to claim 1 including measuring stools physical property properties consisting of stools dimension, shape, consistency and density and forwarding detected data said stools characteristics also to said central control processor to correlate with the stools characteristics and urine bubbles characteristics to provide a comprehensive determination of the health condition of the person.

4. A method according to claim 1 including measuring the loudness of sound of said urine impacting on the water in the toilet and forwarding the detected data to said central control processor for the determination of the health of the person.

5. A method according to claim 4 including measuring temperature of said stools with an IR sensor and forwarding data of said temperature detected to said central control processor to provide additional data for determination of the health condition of the person.

6. A method according claim 5 displaying said health condition of the person on a user interface unit having a visual display.

7. A method according to claim 6 including entering command in a key board of said user interface unit for operating said central control processor.

8. A method according to claim 7 including detecting the presence of the person sitting on the toilet for bowel movement with a motion sensor located at an underside of the toilet seat to activate said central control processor.

\* \* \* \* \*